United States Patent
Zhang et al.

(10) Patent No.: US 12,312,626 B2
(45) Date of Patent: May 27, 2025

(54) METHOD OF ETHANOL FERMENTATION WITH CELLULOSE AT HIGH-SOLIDS LOADING

(71) Applicant: SOUTH CHINA AGRICULTURAL UNIVERSITY, Guangdong (CN)

(72) Inventors: Hongdan Zhang, Guangdong (CN); Xinwen Zhang, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 0 days.

(21) Appl. No.: 18/528,794

(22) Filed: Dec. 5, 2023

(65) Prior Publication Data

US 2024/0182929 A1 Jun. 6, 2024

(30) Foreign Application Priority Data

Dec. 5, 2022 (CN) .......................... 202211547231.5

(51) Int. Cl.
*C12P 7/10* (2006.01)
(52) U.S. Cl.
CPC ..................................... *C12P 7/10* (2013.01)
(58) Field of Classification Search
None
See application file for complete search history.

(56) References Cited

U.S. PATENT DOCUMENTS

2013/0344554 A1* 12/2013 Bleyer ................... B01D 3/002
203/28

FOREIGN PATENT DOCUMENTS

| CN | 106232825 | 12/2016 |
| CN | 113106128 | 7/2021 |
| CN | 113151366 | 7/2021 |

OTHER PUBLICATIONS

Li et al. (Industrial Crops and Products, 62 (2014), pp. 446-452).*
Jixing Hui et al., "Research progress on high-gravity ethanol fermentation techniques", Science & Technology in Chemical Industry, with English abstract, Apr. 25, 2021, pp. 85-88.
Youngmi Kim et al., "Hydrolysis-determining substrate characteristics in liquid hot water pretreated hardwood", Biotechnology and Bioengineering, Apr. 2015, pp. 677-687.
Wenxiang Jin et al., "Tween-80 is effective for enhancing steam-exploded biomass enzymatic saccharification and ethanol production by specifically lessening cellulase absorption with lignin in common reed", Applied Energy, Aug. 1, 2016, pp. 82-90.
Zhi-Hua Liu et al., "Simultaneous saccharification and fermentation of steam-exploded corn stover at high glucan loading and high temperature", Biotechnology for Biofuels, Dec. 4, 2014, pp. 1-16.
Yuzhen Zhang,"Porous solid particles characteristics of biomass and its high-solids enzymatic hydrolysis and fermentation process", Doctoral dissertation for the degree of Doctor of Philosophy in Biochemical Engineering of University of Chinese Academy of Sciences, Dec. 2017, pp. 1-286.
Lei Feng et al., Effects of pre-drying treatments combined with explosion puffing drying on the physicochemical properties, antioxidant activities and flavor characteristics of apples, Food Chemistry, Feb. 15, 2021, pp. 1-9.
Katrina M. Roberts et al., "The effects of water interactions in cellulose suspensions on mass transfer and saccharification efficiency at high solids loadings", Cellulose, Feb. 26, 2011, pp. 759-773.

* cited by examiner

*Primary Examiner* — Hope A Robinson
(74) *Attorney, Agent, or Firm* — JCIPRNET

(57) ABSTRACT

The present invention provides an ethanol fermentation method with cellulose at high-solids loading. The method includes: mixing lignocellulose A treated with NaOH-enhanced ethanol solution and lignocellulose B treated with $AlCl_3$-enhanced ethanol solution, adding water, and mixing to obtain a mixed cellulose solution; then adding a nutrient salt, sterilizing, saccharifying and fermenting, and supplementing mixed cellulose in the fermentation process; and after the completion of material supplementation, mixing the mixed cellulose and water according to a mass ratio of (30-45):100.

6 Claims, No Drawings

METHOD OF ETHANOL FERMENTATION WITH CELLULOSE AT HIGH-SOLIDS LOADING

CROSS-REFERENCE TO RELATED APPLICATION

This application claims the priority benefit of China application serial no. 202211547231.5, filed on Dec. 5, 2022. The entirety of the above-mentioned patent application is hereby incorporated by reference herein and made a part of this specification.

TECHNICAL FIELD

The present invention belongs to the technical field of biomass conversion and utilization, and more particularly, to a method of ethanol fermentation with cellulose at high-solids loading.

BACKGROUND

As a large agricultural country, China is quite rich in biomass resources. However, most agricultural and forestry wastes are disposed by on-site incineration or burial, which not only wastes resources, but also pollutes the ecological environment. Cellulose and hemicellulose are important components in agricultural and forestry wastes, and it is an economically beneficial treatment method to convert them into ethanol through a fermentation technology, which can produce biomass energy while treating agricultural and forestry wastes.

In fermentation production, high ethanol yield can be achieved by increasing the solid concentration of a substrate. In conventional ethanol fermentation, the solid content is in a range of 20% to 24%, while the solid content in high-concentration ethanol fermentation is greater than 30%[1]. The high solid concentration can effectively increase a rate of equipment utilization, reduce the production cost, and reduce the energy consumption in the production process. However, the ethanol yield decreases[3] when the solid content is greater than 15% due to the problems such as poor heat and mass transfer during fermentation with high solid concentrations, unproductive binding of lignin to enzymes, and low water concentrations[2]. At the same time, the concentrations of by-products such as glycerol, acetic acid and lactic acid produced during the reaction will also increase with the increase of solid content, and these by-products will have a certain inhibitory effect on microorganisms for fermentation[4].

High substrate loading fermentation requires a large amount of biomass, and in the process of high-solid enzymatic hydrolysis fermentation, a solid-phase substrate mainly exists in a porous medium structure in a reactor. A large number of studies have proved that the porous structure is an important reason for the enzymatic hydrolysis of lignocellulose, which directly affects the accessibility of enzymes and cellulose substrates[5]. The drying step causes pore size shrinkage due to water loss and heating[6]. Water can affect the progress of enzymatic hydrolysis fermentation, and water that is tightly bound to biomass is often referred to as bound water, which is limited in its degree of freedom and kinetics. Under the condition of high substrate loading, the water binds more closely to organisms, which reduces substrate transport and reaction efficiency[7].

Therefore, it is necessary to develop a method that can effectively improve the efficiency of ethanol fermentation at high solid concentrations.

REFERENCES

[1]. Hui Jixing, Hu Bin, Ning Yanchun, Chen Xihai, Yue Jun, Wang Shuo, Qu Haifeng, Hu Shiyang, Fan Rui. Research progress on high-gravity ethanol fermentation techniques[J]. Chemical Science and Technology, 2021, 29(03): 85-88.

[2]. Kim Y, Kreke T, Ko J K, et al. Hydrolysis-determining Substrate Characteristics in Liquid Hot Water Pretreated Hardwood[J]. Biotechnology and Bioengineering, 2015, 112(4): 677-687.

[3]. Jin W, Chen L, Hu M, et al. Tween-80 is effective for enhancing steam-exploded biomass enzymatic saccharification and ethanol production by specifically lessening cellulase absorption with lignin in common reed [J]. Applied Energy, 2016, 175:82-90.

[4]. Liu Z, Qin L, Zhu J, et al. Simultaneous saccharification and fermentation of steam-exploded corn stover at high glucan loading and high temperature[J]. Biotechnology for Biofuels, 2014, 7(1):167.

[5] Zhang Yuzhen. Porous solid particles characteristics of biomass and its high-solids enzymatic hydrolysis and fermentation process [D]. University of Chinese Academy of Sciences (Institute of Process Engineering, Chinese Academy of Sciences), 2017.

[6]. Feng L, Xu Y, Xiao Y, et al. Effects of pre-drying treatments combined with explosion puffing drying on the physicochemical properties, antioxidant activities and flavor characteristics of apples[J]. Food Chemistry, 2021, 338: 128015.

[7]. Roberts K M, Lavenson D M, Tozzi E J, et al. The effects of water interactions in cellulose suspensions on mass transfer and saccharification efficiency at high solids loadings[J]. Cellulose, 2011, 18(3): 759-773.

SUMMARY OF THE INVENTION

An object of the present invention is to overcome at least one defect of the existing technology, and provide a method of ethanol fermentation with cellulose at high-solids loading.

The present invention adopts the following technical solutions.

A method of ethanol fermentation with cellulose at high-solids loading includes the following steps:

1) pretreatment: mixing lignocellulose A pretreated with NaOH-enhanced ethanol solution and lignocellulose B pretreated with $AlCl_3$-enhanced ethanol solution in a ratio of (2:8) to (6:4), and mixing the mixed cellulose and water in a mass ratio of absolute dry cellulose to water of (7-10):100 to obtain a mixed cellulose solution;

2) sterilization treatment: adding nutrient salts to the mixed cellulose solution in step 1) for sterilization to obtain a sterilized solution;

3) saccharification and fermentation: adding cellulase and a yeast activation solution to the sterilized solution, and then performing simultaneous saccharification and fermentation;

4) material supplementation treatment: supplementing the sterilized mixed cellulose to a fermentation tank in batches or continuously within 6 to 24 h after the start of fermentation; wherein after the completion of material supplementation, a mass ratio of absolute dry cellulose to water is (30-45):100, and a final mixing ratio of the lignocellulose A to the lignocellulose B is (5:5) to (6.5:3.5).

In some embodiments, a moisture content of the mixed cellulose is 0 to 60%.

In some embodiments, a total time of simultaneous saccharification and fermentation is 24 to 200 h.

In some embodiments, the materials are supplemented in batches, i.e., material supplementation is performed for the first time after the start of fermentation for 5 to 7 h; material supplementation is performed for the second time after the start of fermentation for 11 to 13 h; and material supplementation is performed for the last time after the start of fermentation for 22 to 24 h.

In some embodiments, a ratio of the lignocellulose A to the lignocellulose B is (4:6) to (6:4) during the first material supplementation.

In some embodiments, the final mixing ratio of the lignocellulose A to the lignocellulose B is 6:4 after the completion of material supplementation.

In some embodiments, the fermentation in step 3 is performed at a temperature of 30 to 38° C., the pH of 4 to 6 and a rotational speed of 100 to 200 rpm for 0 to 200 h.

In some embodiments, an addition amount of cellulase in step 3 is 10 to 20 FPU/g, and an addition amount of the yeast activation solution is 40 to 60 mL per liter of deionized water.

In some embodiments, temperature of the sterilization in step 2 is 110 to 130° C., and the sterilization lasts for 10 to 30 min.

In some embodiments, a raw material of the lignocellulose is selected from at least one of poplar, eucalyptus, bagasse, corn straws, wheat straws, and corn cobs.

In some embodiments, a preparation method of the lignocellulose A includes: adding 60% (v/v) ethanol aqueous solution to lignocellulosic biomass according to an absolute dry mass-volume ratio of 1 g:10 mL, then adding 10% NaOH, reacting at 195° C. for 30 min, and separating to obtain the lignocellulose A.

In some embodiments, a preparation method of the lignocellulose B includes: adding 60% (v/v) ethanol aqueous solution to lignocellulosic biomass according to an absolute dry mass-volume ratio of 1 g:10 mL, then adding 0.025 mol/L $AlCl_3$, reacting at 200° C. for 10 min, and separating to obtain the lignocellulose B.

The present invention has the following beneficial effects.

According to the method of the present invention, in the mixed fermentation of poplar pretreated with NaOH-enhanced ethanol solution and poplar pretreated with $AlCl_3$-enhanced ethanol solution, the ethanol yield can be significantly increased by different material supplementing ratios in the early and middle stages of fermentation in the condition of a substrate at high-solids loading.

In some examples of the present invention, the pretreated lignocellulose with a certain water content is used, such that the energy consumption for drying the raw materials is reduced, and an original form of fibers can be kept. Therefore, the ethanol concentration can be significantly improved, the fermentation end point can be reached earlier, and the fermentation time is saved.

DETAILED DESCRIPTION OF THE INVENTION

A method of ethanol fermentation with cellulose at high-solids loading includes the following steps:

1) pretreatment: mixing lignocellulose A pretreated with NaOH-enhanced ethanol solution and lignocellulose B pretreated with $AlCl_3$-enhanced ethanol solution in a ratio of (2:8) to (6:4), and mixing the mixed cellulose and water in a mass ratio of absolute dry cellulose to water of (7-10):100 to obtain a mixed cellulose solution;
2) sterilization treatment: adding nutrient salts to the mixed cellulose solution in step 1) for sterilization to obtain a sterilized solution;
3) saccharification and fermentation: adding cellulose and a yeast activation solution to the sterilized solution, and then performing simultaneous saccharification and fermentation;
4) material supplementation treatment: supplementing the sterilized mixed cellulose to a fermentation tank in batches or continuously within 6 to 24 h after the start of fermentation; wherein after the completion of material supplementation, a mass ratio of absolute dry cellulose to water is (30-45):100, and a final mixing ratio of the lignocellulose A to the lignocellulose B is (5:5) to (6.5:3.5).

The nutrient salts are commonly used nutrient salts to ensure the needs of yeast proliferation.

In some embodiments, a moisture content of the mixed cellulose is 0 to 60%.

In some embodiments, a total time of simultaneous saccharification and fermentation is 24 to 200 h. The specific fermentation time may be adjusted correspondingly according to the specific fermentation results.

The timing of material supplementation may be determined based on the viscosity of ferments. In some embodiments, the materials are supplemented in batches, i.e., material supplementation is performed for the first time after the start of fermentation for 5 to 7 h; material supplementation is performed for the second time after the start of fermentation for 11 to 13 h; and material supplementation is performed for the last time after the start of fermentation for 22 to 24 h. The amount of each material supplementation may be the same or different.

In some embodiments, a ratio of the lignocellulose A to the lignocellulose B is (4:6) to (6:4) during the first material supplementation. Experimental data show that the fermentation can be prompted well.

In some embodiments, the final mixing ratio of the lignocellulose A to the lignocellulose B is 6:4 after the completion of material supplementation. Experimental data show that this mixing ratio can shorten the total fermentation time while obtaining higher ethanol concentrations.

In some embodiments, the fermentation in step 3 is performed at a temperature of 30 to 38° C., the pH of 4 to 6 and a rotational speed of 100 to 200 rpm for 0 to 200 h.

In some embodiments, an addition amount of the cellulase in step 3 is 10 to 20 FPU/g, and an addition amount of the yeast activation solution is 40 to 60 mL per liter of deionized water.

In some embodiments, temperature of the sterilization in step 2 is 110 to 130° C., and the sterilization lasts for 10 to 30 min.

In some embodiments, a raw material of the lignocellulose is selected from at least one of poplar, eucalyptus, bagasse, corn straws, wheat straws, and corn cobs.

In some embodiments, a preparation method of the lignocellulose A includes: adding 60% (v/v) ethanol aqueous solution to lignocellulosic biomass according to an absolute dry mass-volume ratio of 1 g:10 mL, then adding 10% NaOH, reacting at 195° C. for 30 min, and separating to obtain the lignocellulose A. Of course, the lignocellulose A may also be obtained using other similar conditions.

In some embodiments, a preparation method of the lignocellulose B includes: adding 60% (v/v) ethanol aqueous solution to lignocellulosic biomass according to an absolute dry mass-volume ratio of 1 g:10 mL, then adding 0.025 mol/L $AlCl_3$, reacting at 200° C. for 10 min, and separating to obtain the lignocellulose B. Of course, the lignocellulose B may also be obtained using other similar conditions.

The following disclosure provides many different embodiments or examples that can be used to implement different schemes.

For the sake of convenient comparison, the poplar raw material used is air-dried and crushed, and its component content includes 43.05% of cellulose, 13.90% of hemicellulose and 23.65% of lignin.

The yeast activation solution is prepared as follows: weighing 1 g of glucose, 1 g of peptone, and 0.5 g of yeast extract, and dissolving them in 50 mL of deionized water, adding 3.3 g of *Saccharomyces cerevisiae*, and activating at 34° C. on a 150 rpm shaker for 60 min.

Example 1 A Method for Improving the Fermentation Efficiency by Different Material Supplementation Ratios at High-Solids Loading S1. adding 60% (v/v) ethanol aqueous solution to raw poplar according to an absolute dry mass-volume ratio of 1 g:10 mL, then adding 10% NaOH, reacting at 195° C. for 30 min, and separating to obtain poplar pretreated with NaOH-enhanced ethanol solution, that is, lignocellulose A;

S2. adding 60% (v/v) ethanol aqueous solution to raw poplar according to an absolute dry mass-volume ratio of 1 g:10 mL, then adding 0.025 mol/L $AlCl_3$, reacting at 200° C. for 10 min, and separating to obtain poplar pretreated with $AlCl_3$-enhanced ethanol solution, that is, lignocellulose B;

S3. drying the two kinds of pretreated poplar to be used for 6 h to 24 h in an oven at 55° C. until they were absolutely dry, so as to obtain a dry material with the moisture content of 0%;

S4. mixing poplar pretreated with NaOH and poplar pretreated with $AlCl_3$ in a ratio of 5:5, and adding water to the mixed pretreated poplar to obtain a pretreated poplar-water mixture, wherein a mass ratio of absolute dry poplar to water is 8:100;

S5. adding nutrient salts to the pretreated poplar-water mixture in step S4, adjusting pH to 4.8, and sterilizing at 121°C for 20 min to obtain a sterilized poplar mixture;

S6. adding 15 FPU/g cellulase corresponding to the substrate concentration of 32% and adding 50 ml/L deionized water yeast activation solution to the sterilized poplar mixture, and performing simultaneous saccharification and fermentation at 34° C. and at a rotational speed of 130 rpm/min;

S7. adding the absolutely dry pretreated wood fiber mixture with a mass of 8% of water at 6 h, 12 h and 24 h after the start of fermentation in step S6 respectively: wherein the viscosity was reduced to 56 mPa·S after 6 h of fermentation, supplementing a dry material of the sterilized mixed pretreated poplar which has the same ratio as that in S4, and supplementing one-half of the remaining dry material of the sterilized mixed pretreated poplar at 12 h and 24 h after the start of fermentation in sequence, wherein a final mixing ratio of the lignocellulose A to the lignocellulose B is 6:4 after the completion of material supplementation.

Example 2 A Method for Improving Ethanol Efficiency Through Mixed Fermentation This example differs from Example 1 in that: at 0 h (that is, the step S4) and 6 h, a mixing ratio of the poplar pretreated with NaOH-enhanced ethanol solution to the poplar pretreated with $AlCl_3$-enhanced ethanol solution is 4:6, and its viscosity decreased to 48 mPa·S after 6 h of fermentation.

Example 3 A Method for Improving Ethanol Efficiency Through Mixed Fermentation This example differs from Example 1 in that: at 0 h (that is, the step S4) and 6 h, a mixing ratio of the poplar pretreated with NaOH-enhanced ethanol solution to the poplar pretreated with $AlCl_3$-enhanced ethanol solution is 2:8, and its viscosity decreases to 40 mPa·S after 6 h of fermentation.

Comparative Example 1

This example differs from Example 1 in that: at 0 h (that is, the step S4) and 6 h, a mixing ratio of the poplar pretreated with NaOH-enhanced ethanol solution to the poplar pretreated with $AlCl_3$-enhanced ethanol solution is 6:4, and its viscosity was still up to 60 mPa·S after 6 h of fermentation.

Table 1 shows the mixing ratios of the lignocellulose A to the lignocellulose B at different feeding time of Examples 1-3 and Comparative example 1.

TABLE 1

Mixing ratios of the lignocellulose A to the lignocellulose B at different feeding time of Examples 1-3 and Comparative example 1

| | Mixing ratio of the lignocellulose A to the lignocellulose B | | | |
|---|---|---|---|---|
| Feeding time | Example 1 | Example 2 | Example 3 | Comparative example 1 |
| 0 h | 5:5 | 4:6 | 2:8 | 6:4 |
| 6 h | 5:5 | 4:6 | 2:8 | 6:4 |
| 12 h | 7:3 | 8:2 | 10:0 | 6:4 |
| 24 h | 7:3 | 8:2 | 10:0 | 6:4 |
| Final | 6:4 | 6:4 | 6:4 | 6:4 |

Experimental Assay

The concentrations of ethanol in fermentation broth at the time of fermentation from 6 h to 144 h in the Examples 1-3 and the comparative example 1 were determined by high performance liquid chromatography, and the specific results are shown in Table 2:

TABLE 2

Concentrations of ethanol in fermentation broth (g/L) at the time of fermentation from 6 to 144 h in different treatment groups

| | Example 1 | Example 2 | Example 3 | Comparative example 1 |
|---|---|---|---|---|
| 6 h | 24.17 | 26.50 | 27.29 | 23.12 |
| 12 h | 33.10 | 35.66 | 36.08 | 32.57 |
| 24 h | 44.76 | 46.85 | 48.02 | 45.44 |
| 48 h | 55.75 | 58.26 | 60.88 | 54.75 |
| 72 h | 58.25 | 59.69 | 63.34 | 56.80 |
| 96 h | 56.77 | 60.39 | 64.08 | 57.13 |

TABLE 2-continued

Concentrations of ethanol in fermentation broth (g/L) at the time of fermentation from 6 to 144 h in different treatment groups

|  | Example 1 | Example 2 | Example 3 | Comparative example 1 |
|---|---|---|---|---|
| 120 h | 57.19 | 58.63 | 63.22 | 54.43 |
| 144 h | 55.90 | 58.39 | 62.95 | 56.51 |

It can be seen from the results in Table 2 that under the condition that a substrate concentration (32%) and a final ratio (6:4) are consistent, the ethanol concentrations with different material supplementation ratios are significantly improved; and the maximum ethanol concentration reaches 64.08 g/L when supplementing at 0 h and 6 h of the fermentation according to a ratio of 2:8 (Example 3), which is increased by 12.16%, compared to the maximum ethanol concentration being 57.13 g/L when supplementing at 0 h and 6 h according to a ratio of 6:4 (the comparative example 1). It can be seen that according to the method of the present invention, the yield of ethanol fermentation for poplar at high-solids loading can be effectively increased.

Example 4

S1. adding 60% (v/v) ethanol aqueous solution to raw poplar according to an absolute dry mass-volume ratio of 1 g:10 mL, then adding 10% NaOH, reacting at 195° C. for 30 min, and separating to obtain poplar pretreated with NaOH-enhanced ethanol solution;

S2. adding 60% (v/v) ethanol aqueous solution to raw poplar according to an absolute dry mass-volume ratio of 1 g:10 mL, then adding 0.025 mol/L $AlCl_3$, reacting at 200° C. for 10 min, and separating to obtain poplar pretreated with $AlCl_3$-enhanced ethanol solution;

S3. drying the two kinds of pretreated poplar to be used for 6 h to 24 h in an oven at 55° C. to dryness, so as to obtain a dry material with a moisture content of 50%;

S4. mixing poplar pretreated with NaOH and poplar pretreated with $AlCl_3$ in a ratio of 2:8, and adding water to the mixed pretreated poplar to obtain a pretreated poplar-water mixture, wherein a mass ratio of absolute dry poplar to water is 8:100;

S5. adding nutrient salts to the pretreated poplar-water mixture in step S3, adjusting pH to 4.8, and sterilizing at 121°C for 20 min to obtain a sterilized poplar mixture;

S6. adding 15 FPU/g cellulase corresponding to the substrate concentration of 32% and adding 50 ml/L deionized water yeast activation solution to the sterilized poplar mixture, and performing simultaneous saccharification and fermentation at 34° C. and at a rotational speed of 130 rpm/min;

S7. after the start of fermentation in S6, supplementing a dry material according to one-third of the total amount of remaining mixed poplar at 6 h, 12 h and 24 h, wherein the sterilized mixed dry material in the same ratio as in S4 was supplemented at 6 h, and one-half of the remaining sterilized mixed dry material was sequentially supplemented at 12 h and 24 h.

Example 5: A Method for Improving Fermentation Efficiency of High-Concentration Ethanol by Increasing Water Content This example differs from Example 4 in that: the water content of the dry material obtained in step S3 is 25%.

Example 6: A Method for Improving Fermentation Efficiency of High-Concentration Ethanol by Increasing Water Content This example differs from Example 4 in that: the total substrate concentration is 38%, and in step S6, 15 FPU/g cellulase corresponding to the substrate concentration of 38% was added to the sterilized poplar mixture.

Example 7: A Method for Improving Fermentation Efficiency of High-Concentration Ethanol by Increasing Water Content This example differs from Example 4 in that: the total substrate concentration is 44%, and in step S6, 15 FPU/g cellulase corresponding to the substrate concentration of 44% was added to the sterilized poplar mixture.

Example 8

This example differs from Example 4 in that: the water content of the dry material obtained in step S3 is 0%.
Comparison of Fermentation Under Different Conditions
The concentrations of ethanol in fermentation broth at the time of fermentation from 6 h to 192 h in Examples 4 to 8 were determined by high performance liquid chromatography, and the specific results are shown in Table 3:

TABLE 3

Concentrations of ethanol in fermentation broth (g/L) at the time of fermentation from 6 h to 192 h in different treatment groups

|  | Example 4 | Example 5 | Example 6 | Example 7 | Example 8 |
|---|---|---|---|---|---|
| 6 h | 31.94 | 27.37 | 27.77 | 20.24 | 27.29 |
| 12 h | 46.45 | 37.69 | 42.88 | 33.03 | 36.08 |
| 24 h | 54.01 | 47.43 | 58.89 | 58.66 | 48.02 |
| 48 h | 63.91 | 60.31 | 67.45 | 70.41 | 60.88 |
| 72 h | 69.74 | 63.02 | 77.73 | 79.20 | 63.34 |
| 96 h | 71.83 | 63.13 | 80.68 | 81.57 | 64.08 |
| 120 h | 74.85 | 66.54 | 80.86 | 82.13 | 63.22 |
| 144 h | 73.62 | 67.56 | 81.80 | 84.60 | 62.95 |
| 168 h | 74.94 | 69.22 | 81.76 | 86.60 | 62.48 |
| 192 h | 74.57 | 68.07 | 80.72 | 83.41 | 61.67 |

As can be seen from the results in Table 3, the ethanol concentration obtained by material supplementation in batches and simultaneous saccharification and fermentation has significantly increased as the moisture content of the dry material increases. The maximum ethanol concentration in the case that the dry material has the moisture content of 0% is 64.08 g/L (Example 8), while the maximum ethanol concentration in the case that the dry material has the moisture content of 25% is 69.22 g/L, which is increased by 8.02%; and the maximum ethanol concentration in the case that the dry material has the moisture content of 50% is 74.94 g/L, which is increased by 16.95%. Based on the moisture content of 50%, the substrate concentration is increased, the maximum ethanol concentration under the substrate concentration of 38% is 81.80 g/L, and the maximum ethanol concentration under the substrate concentration of 44% is 86.60 g/L. It can be seen that according to the method of the present invention, the fermentation efficiency of high-concentration ethanol for poplar can be effectively improved.

The above content is a further detailed description of the present invention, but cannot be regarded as any limitation to the specific implementation of the present invention. For a person of ordinary skill in the art to which the present invention belongs, simple deductions or replacements without departing from the concept of the present invention all fall within the protection scope of the present invention.

What is claimed is:

1. An ethanol fermentation method with cellulose at high-solids loading, comprising the following steps:
   1) pretreatment: mixing a lignocellulose A pretreated with a sodium hydroxide-enhanced ethanol solution and a lignocellulose B pretreated with an aluminum chloride-enhanced ethanol solution in a ratio of (2:8) to (4:6) to obtain a mixed cellulose having a moisture content of 50%, and mixing the mixed cellulose and water according to a mass ratio of absolute dry cellulose to water of (7-10):100 to obtain a mixed cellulose solution;
   2) sterilization treatment: adding nutrient salts to the mixed cellulose solution in step 1) for sterilization to obtain a sterilized solution;
   3) saccharification and fermentation: adding cellulase and a yeast activation solution to the sterilized solution, and then performing simultaneous saccharification and fermentation, wherein a total time of simultaneous saccharification and fermentation is 24 to 200 hours;
   4) material supplementation treatment: within 6 to 24 hours after start of fermentation, supplementing a sterilized mixed cellulose to a fermentation tank in batches, wherein when the supplementing is completed, a mass ratio of absolute dry cellulose to water is (30-45):100, and a final mixing ratio of the lignocellulose A to the lignocellulose B is (5:5) to (6.5:3.5);
   and wherein the supplementing comprises a first material supplementation, a second material supplementation and a third material supplementation; 6 to 7 hours after the start of fermentation, the first material supplementation is performed to allow a ratio of the lignocellulose A to the lignocellulose B to be (4:6) to (6:4); 11 to 13 hours after the start of fermentation, the second material supplementation is performed; and 22 to 24 hours after the start of fermentation, and the third material supplementation is performed.

2. The method of claim 1, wherein a raw material of the lignocellulose is selected from at least one of poplar, eucalyptus, bagasse, corn straws, wheat straws, or corn cobs.

3. The method of claim 1, wherein the sterilization in step 2) is at a temperature of 110 to 130° C., and lasts for 10 to 30 minutes.

4. The method of claim 1, wherein the fermentation in step 3) is performed at a temperature of 30 to 38° C., a pH of 4 to 6, and a rotational speed of 100 to 200 rpm.

5. The method of claim 1, wherein the cellulase added in step 3) is 10 to 20 FPU/g, and the yeast activation solution added is 40 to 60 mL per liter of deionized water.

6. The method of claim 1, wherein the final mixing ratio of the lignocellulose A to the lignocellulose B is 6:4 when the supplementing is completed.

* * * * *